(12) United States Patent
Kusunoki et al.

(10) Patent No.: US 8,186,349 B2
(45) Date of Patent: May 29, 2012

(54) TRACHEOSTOMY TUBE

(75) Inventors: Takao Kusunoki, Fukuroi (JP); Masaki Moriyama, Tokyo (JP)

(73) Assignee: Covidien AG, Neuhausen am Rheinfall (CH)

( * ) Notice: Subject to any disclaimer, the term of this patent is extended or adjusted under 35 U.S.C. 154(b) by 1240 days.

(21) Appl. No.: 11/576,802

(22) PCT Filed: Oct. 5, 2005

(86) PCT No.: PCT/EP2005/010729
§ 371 (c)(1),
(2), (4) Date: Nov. 5, 2007

(87) PCT Pub. No.: WO2006/037626
PCT Pub. Date: Apr. 13, 2006

(65) Prior Publication Data
US 2008/0163870 A1 Jul. 10, 2008

(30) Foreign Application Priority Data
Oct. 5, 2004 (JP) ................................. 2004-292545

(51) Int. Cl.
*A61M 11/00* (2006.01)

(52) U.S. Cl. .............................. 128/207.14; 128/207.15

(58) Field of Classification Search ............ 128/207.14–207.18, 207.29; 606/108, 194–195; 600/184; 604/96.01
See application file for complete search history.

(56) References Cited

U.S. PATENT DOCUMENTS

| 4,100,309 A | 7/1978 | Micklus et al. |
| 4,315,505 A * | 2/1982 | Crandall et al. ......... 128/200.26 |
| 4,361,107 A | 11/1982 | Gereg |

(Continued)

FOREIGN PATENT DOCUMENTS

JP 61209669 A 9/1986

(Continued)

OTHER PUBLICATIONS

Blunt, Mark C., et al., Gel Lubrication of the Tracheal Tube Cuff Reduces Pulmonary Aspiration, Using Silcone Cuff, Biosiences Information Service, Database Biosis, XP002376266, Mar. 2000, 2 pp., Philadelphia, PA, USA.

(Continued)

*Primary Examiner* — Steven Douglas
(74) *Attorney, Agent, or Firm* — Senniger Powers LLP

(57) ABSTRACT

To provide a tracheostomy tube which can be easily attached to and detached from an incision site and in which sputum or the like does not readily longer, a tracheostomy tube A includes a lumen body 10 having an airway securing lumen 10*b*, a connector section 11 formed at the base end portion of the lumen body 10, and a cuff 13 which is formed on the outer circumference of the tip end portion of the lumen body 10 and which can be expanded and contracted. A circumferential wall 10*a* of the lumen body 10 defines a cuff-expanding lumen 15 which puts the surface portion of the connector section 11 in communication with the inside of the cuff 13. it also defines a suction lumen 14 allowing the surface portion of the connector section 11 to communicate with the surface portion of the lumen body 10. A coating layer exhibiting surface lubricity in moisture is formed on the surface of the tracheostomy tube A and the inner surface of the lumen body 10 in which the airway securing lumen 10*b* is formed.

12 Claims, 1 Drawing Sheet

U.S. PATENT DOCUMENTS

| | | | |
|---|---|---|---|
| 4,729,914 A * | 3/1988 | Kliment et al. | 428/35.7 |
| 5,067,496 A * | 11/1991 | Eisele | 128/207.15 |
| 5,285,777 A * | 2/1994 | Beckwith | 128/207.15 |
| 5,932,299 A | 8/1999 | Katoot | |
| 6,242,041 B1 | 6/2001 | Katoot et al. | |
| 6,460,540 B1 * | 10/2002 | Klepper | 128/207.14 |
| 6,575,158 B1 | 6/2003 | Chelly et al. | |
| 6,716,895 B1 | 4/2004 | Terry | |
| 6,725,862 B2 | 4/2004 | Klinberg et al. | |
| 6,796,309 B2 | 9/2004 | Nash et al. | |
| 7,008,979 B2 | 3/2006 | Schottman et al. | |
| 2003/0049300 A1 | 3/2003 | Terry | |
| 2004/0043052 A1 | 3/2004 | Hunter et al. | |
| 2004/0049222 A1 | 3/2004 | Schaeffer et al. | |
| 2005/0165366 A1 | 7/2005 | Brustad et al. | |

FOREIGN PATENT DOCUMENTS

| | | |
|---|---|---|
| JP | 06007426 A | 1/1994 |
| JP | 2001212244 A | 8/2001 |
| JP | 2003093512 | 9/2001 |
| JP | 2003093512 A | 4/2003 |
| WO | 8907520 A1 | 8/1989 |
| WO | 9924174 A1 | 5/1999 |
| WO | 9944665 A2 | 9/1999 |
| WO | 03099346 A2 | 12/2003 |
| WO | 2004002562 A2 | 1/2004 |

OTHER PUBLICATIONS

Byhahn, C. et al., The Prevention of Pulmonary Aspiration with Control of Tracheal Wall Pressure, Biosiences Information Service, Database Biosis, XP002376115, Aug. 2001, 2 pp., Philadelphia, PA, USA.

Yount, P. J. et al., Ciaglia Blue Rhino: A Modified Technique of Percutaneous Dilatational Tracheostomy, Technique and Early Results, Database Medline, XP002376116, US National Library of Medicine (NLM), Dec. 2000, 1 pg., Bethesda, MD, USA.

* cited by examiner

TRACHEOSTOMY TUBE

CROSS-REFERENCE TO RELATED APPLICATIONS

This application claims priority from PCT/EP2005/010729 (published as WO 2006/037626), filed on Oct. 5, 2005. PCT/EP2005/010729 claims priority from JP2004-292545, filed on Oct. 5, 2004. The entirety of the disclosures of PCT/EP2005/010729 and JP2004-292545 are hereby incorporated by reference.

TECHNICAL FIELD

The present invention relates to a tracheostomy tube used for a patient having an impaired or deteriorated respiration function.

BACKGROUND OF THE INVENTION

Conventionally, patients having a deteriorated respiration function have been subjected to such a treatment as performing a tracheostomy and inserting a tracheostomy tube into the incision site. As a result, air can be sent directly to the lungs through a trachea from the outside, not through a throat or a nose, or can be sent to the outside through the trachea from the lungs (for example, see Patent Document 1, as discussed below). In such a tracheostomy tube, a connector section is provided at the base end portion of a lumen body in which an airway securing lumen is formed from the base end portion to the tip end portion and a cuff which is expandable and contractible is provided on the outer circumference of the tip end portion of the lumen body.

A cuff-expanding lumen allowing one side of the surface of the connector section to communicate with the inside of the cuff is formed in the wall of the lumen body and thus the cuff can be expanded by injecting air into the cuff through the cuff-expanding lumen from the connector section. The expanded cuff allows the tracheostomy tube to be supported by a predetermined portion of the trachea in a state that the trachea is clogged.

A suction lumen allowing the other side of the surface of the connector section to communicate with a predetermined portion of the surface of the lumen body is formed in the wall of the lumen body and thus sputum or the like accumulated between the lumen body and the trachea can be discharged externally through the suction lumen by allowing the connector section side to perform an suction. When the tracheostomy tube having the above-mentioned structure is attached to the incision site of a patient, a lubricant such as a jelly is applied to the surface of the lumen body or the cuff. As a result, the operations of attaching the tracheostomy tube to the incision site of a patient, and detaching the tracheostomy tube from the incision site when it should be replaced with the lapse of time after the attachment, can be performed smoothly.

Above mentioned Patent Document 1 is Japanese Unexamined Patent Application Publication No. 2003-93512.

However, in the tracheostomy tube described in Patent Document 1, there is a problem that the operation of applying a lubricant to the lumen body or the cuff is troublesome when the tracheostomy tube is attached to the trachea. Further, there is a problem in that sputum or foods can be easily accumulated inside the tracheostomy tube.

The present invention is contrived to solve the problems. It is an object of the present invention to provide a tracheostomy tube which can be smoothly attached to or detached from the incision site and in which sputum or the like is not easily accumulated therein.

In order to accomplish the above-mentioned object, according to an aspect of the present invention, there is provided a tracheostomy tube comprising: a lumen body having an airway securing lumen extending from a base end portion to a tip end portion; a connector section formed at the base end portion of the lumen body; a cuff which is formed on the outer circumference of the tip end portion of the lumen body and which is expandable and contractible; a cuff-expanding lumen which is formed in the wall of the lumen body and which allows the surface portion of the connector section to communicate with the inside of the cuff; and a suction lumen which is formed in the wall of the lumen body and which allows the surface portion of the connector section to communicate with the surface portion of the lumen body, wherein a coating layer exhibiting surface lubricity in moisture is formed on the surface of the tracheostomy tube and the inner surface of the lumen body in which the airway securing lumen is formed.

In the tracheostomy tube having the above-mentioned structure, the coating layer exhibiting the surface lubricity in moisture is formed on the surface of the tracheostomy tube. As a result, when the tracheostomy tube is fitted to or detached from the incision site of a patient, it is possible to easily perform the operation of fitting or detachment by performing a simple operation such as dipping the surface of the tracheostomy tube into water. The coating layer exhibiting the surface lubricity in moisture is formed on the inner surface of the lumen body in which the airway securing lumen is formed.

As a result, when the inner surface of the lumen body gets wet by vapor or spit at the time of the patient's respiration, the surface lubricity is exhibited. Accordingly, sputum or the like is not easily attached to the inner surface of the lumen body. As a result, it is possible to prevent sputum or foods from being accumulated in the lumen body. In this case, the surface of the tracheostomy on which the coating layer is formed includes at least the surface of the lumen body or the cuff, that is, a portion coming in contact with the incision site of the patient when the tracheostomy tube is fitted or detached.

In the tracheostomy tube according an embodiment of to present invention, the coating layer may be made of a mixture of methylvinyl ether maleic anhydride copolymer and fluorine-containing acryl urethane silicon resin.

The mixture exhibits the surface lubricity in moisture and thus allows the surface of the tracheostomy tube or the inner surface of the lumen body in which the airway securing lumen is formed to easily slide. Accordingly, since the insertion resistance when the tracheostomy tube is inserted into the incision site becomes small, the tracheostomy tube can be easily fitted. Similarly, the tracheostomy tube can be easily detached from the incision site and foreign substances such as sputum is not easily accumulated in the tracheostomy tube. The coating layer made of the mixture can be formed through a simple process such as dipping the constituent base members of the tracheostomy tube in the mixture, without performing any pretreatment such as introduction of a function group, thereby giving the lubricity to the constituent base members of the tracheostomy tube. Since the mixture is low in cost and is widely used, the mixture is easily available.

In the tracheostomy tube according to an embodiment of the present invention, the coating layer may be made of a mixture of methyl vinyl ether maleic anhydride copolymer and polyether-block-amide. Accordingly, the lubricity can be given to the constituent base members of the tracheostomy tube by the use of a simple process. The coating layer can be formed out of a material which is low in cost, is easily available, and is widely used. By using the mixture, it is possible to obtain the coating layer having high durability.

In the tracheostomy tube according an embodiment of to present invention, the coating layer may be made of a mixture including polyisocyanate and a mixture including polyvinyl pyrrolidone. Since the coating layer made of the mixtures can be formed on the surface of a constituent base member made of any polyurethane resin, it is possible to form the coating layer having excellent lubricity by making the constituent base members of the tracheostomy tube out of predetermined polyurethane resin.

In the tracheostomy tube according to the present invention, the coating layer may be formed by depositing a mixture including a solvent in which a material of the tracheostomy tube is poorly soluble. In this case, it is preferable that the main component of the solvent is alcohol such as 2-propanol or ethanol. As a result, it is possible to form the coating layer having excellent lubricity on the surface of the tracheostomy tube or the inner surface of the lumen body in which the airway securing lumen is formed, without melting the respective base members of the tracheostomy tube, specifically, the cuff.

SUMMARY OF THE INVENTION

In one aspect of the present invention, a tracheostomy tube is provided. The tracheostomy tube comprises a lumen body having a circumferential wall which defines an airway securing lumen, the circumferential wall having an inner surface, an outer surface, a base end portion, and a tip end portion, wherein the airway securing lumen extends from the base end portion to the tip end portion; a connector section having a surface portion, which is formed at the base end portion of the lumen body; a cuff having an inner surface and an outer surface, which is formed on the outer surface of the tip end portion of the lumen body and which is expandable and contractible; a cuff-expanding lumen which is formed in the circumferential wall of the lumen body and which allows the surface portion of the connector section to communicate with the inner surface of the cuff; and a suction tube which is formed in the circumferential wall of the lumen body and which allows the surface portion of the connector section to communicate with the outer surface of the lumen body; wherein a coating layer exhibiting surface lubricity in moisture is formed on the outer surface of the lumen body, the outer surface of the cuff, and the inner surface of the lumen body in which the airway securing lumen is formed.

In another aspect, the tracheostomy tube comprises a lumen body having a circumferential wall which defines an airway securing lumen, the circumferential wall having an securing lumen extends from the base end portion to the tip end portion; a connector section having a surface portion, which is formed at the base end portion of the lumen body; a cuff having an inner surface and an outer surface, which is formed on the outer surface of the tip end portion of the lumen body and which is expandable and contractible; a cuff-expanding lumen which is formed in the circumferential wall of the lumen body and which allows the surface portion of the connector section to communicate with the inner surface of the cuff; and a suction tube which is formed in the circumferential wall of the lumen body and which allows the surface portion of the connector section to communicate with the outer surface of the lumen body; wherein a coating layer exhibiting surface lubricity in moisture is formed on the outer surface of the lumen body, the outer surface of the cuff, and the inner surface of the lumen body in which the airway securing lumen is formed, the coating layer comprising a polymer selected from the group consisting of fluorine-containing acryl urethane silicon resin, polyether-block-amide, and polyisocyanate.

DETAILED DESCRIPTION

Figure 1:
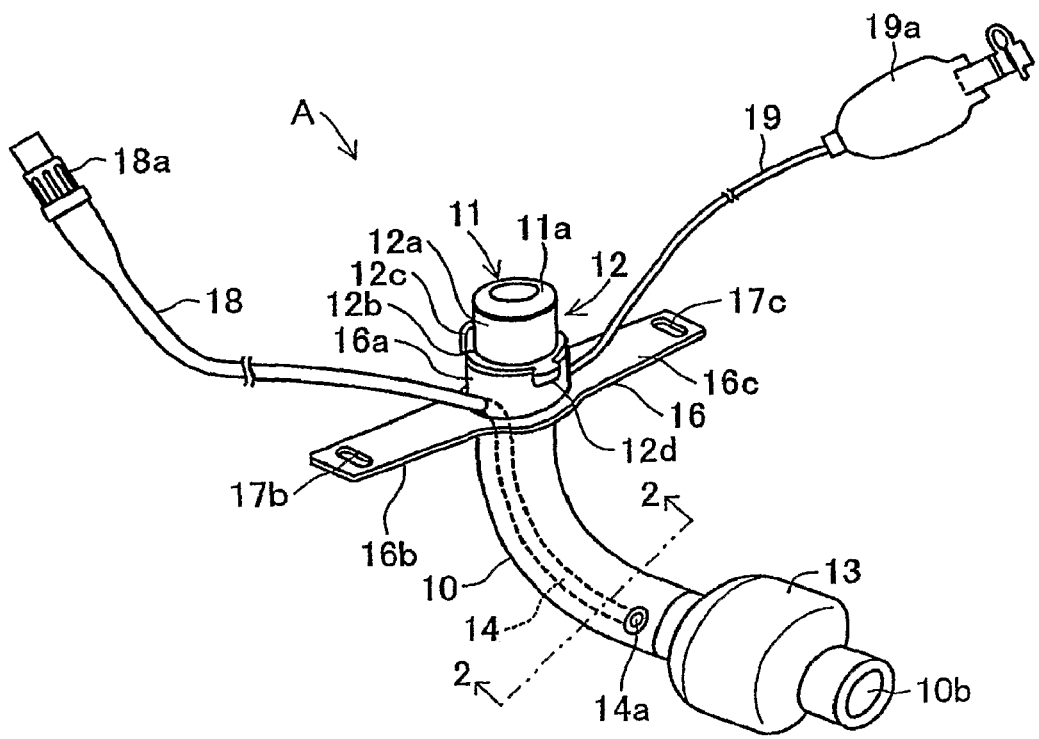
FIG. 1 is a perspective view of a tracheostomy tube.

Hereinafter, an embodiment of the present invention will be described with reference to the accompanying drawings. The tracheostomy tube A of FIG. 1 includes a lumen body 10 made of a polyurethane resin, a connector section 11 fitted to the base end portion (the top end portion in FIG. 1) of the lumen body 10, a coupling section 12 fitted to the connector section 11, and a cuff 13 formed on the outer circumferential surface of the tip end portion (the bottom end portion in FIG. 1) of the lumen body 10.

Figure 2:
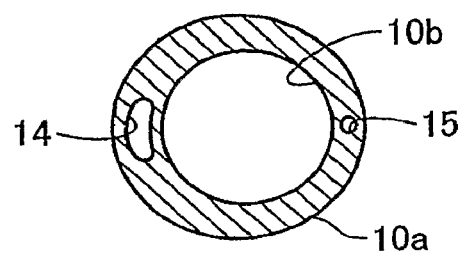
FIG. 2 is a cross-sectional view taken along Line 2-2 of FIG. 1.

The lumen body 10 is formed of a tube of which the axis line extending from the base end portion to the tip end portion is curved approximately at 90°. The circumferential wall 10a has a non-uniform thickness such that one side in the circumferential direction is thick and the other side is thin, as shown in FIG. 2. The inside of the lumen body 10 serves as an airway securing lumen 10b which allows the base end portion of the lumen body 10 to communicate with the tip end portion thereof. In the thick portion of the circumferential wall 10a, a suction lumen 14 is formed from the base end portion of the lumen body 10 to the tip end portion (to the vicinity of the cuff 13). In the thin portion of the circumferential wall 10a, a cuff-expanding lumen 15 is formed from the base end portion of the lumen body 10 to the inside of the cuff 13.

The suction lumen 14 and the cuff-expanding lumen 15 are opposed to each other in the circumferential wall 10a. The cross-section of the suction lumen 14 has a shape that an ellipse is curved along the circumference of the circumferential wall 10a and the cross-section of the cuff expanding lumen 15 has a circular shape with a small diameter. The tip end portion of the suction lumen 14 is opened to the outer circumferential surface of the lumen body 10 to form an opening 14a.

The connector section 11 formed at the base end portion of the lumen body 10 includes a cylindrical portion 11a at the upper side and a fixing portion 16 at the lower side. A coupling section 12 is attached to the outer circumferential surface of the cylindrical portion 11a in an axially rotatable manner. The coupling section 12 includes an cylindrical body 12a provided on the outer circumference of the cylindrical portion 11a, a flange portion 12b formed on the circumferential edge of the lower end of the body 12a, and a pair of hooking pieces 12c and 12d protruded from both sides of the flange portion 12b. Each of the hooking pieces 12c and 12d has a hook shape extending in the horizontal direction and then extending toward the lower side and has a structure to which a belt or the like of another instrument (not shown) can be hooked. At the time of the hooking operation, the coupling section 12 can rotate in the axial rotation direction.

A portion between the upper end of the cylindrical portion 11a and the fixing portion 16 is formed as a small-diameter portion and the coupling section 12 is attached to the outer circumference of the small-diameter portion. The fixing portion 16 includes a cylindrical axis portion 16a connected to the lower end of the cylindrical portion 11a and a pair of plate-shaped arms 16b and 16c extending from both lower ends of the axis portion 16a approximately in the horizontal direction. Elliptical holes 17b and 17c extending in the width direction of the respective arms 16b and 16c are formed in the tip end portions of the arms 16b and 16c. The holes 17b and 17c serve to transmit a belt for attaching the tracheostomy tube A to a patient.

A suction-lumen tube 18 is connected to the side of the axis portion 16a close to the arm 16b and a cuff tube 19 is connected to the side of the axis portion 16a close to the arm-16c. The suction-lumen tube 18 communicates with the upper end portion of the suction lumen 14 and the inner diameter of the suction-lumen tube 18 is set approximately equal to the inner diameter of the suction lumen 14. The cuff tube 19 communicates with the upper end portion of the cuff expanding lumen 15 and the inner diameter of the cuff tube 19 is set approximately equal to the inner diameter of the cuff expanding lumen 15.

The tip end portion of the suction-lumen tube 18 is provided with a suction opening 18a and sputum or foods accumulated in the vicinity of the opening 14a can be discharged externally from the suction opening 18a through the suction lumen 14 by coupling a suction machine (not shown) to the suction opening 18a and performing a suction. The tip end portion of the cuff tube 19 is provided with an air injection portion 19a and air can be injected into the cuff 13 through the cuff-expanding lumen 15 by injecting the air into the cuff tube 19 from the air injection portion 19a.

The cuff 13 is made of a thin film formed on the outer circumferential surface of the tip end portion of the lumen body 10 and serves to form a hollow portion of a tire shape by injecting the air into the space formed along with the outer circumferential surface of the lumen body 10. That is, the cuff 13 is expanded by injecting the air through the cuff tube 19 and the cuff 13 is contracted by withdrawing and discharging the air therethrough. When the cuff 13 is expanded in a state that the tracheostomy tube A is inserted into the trachea of a patient, the tracheostomy tube A is supported in the trachea in a state that the space between the trachea and the tracheostomy tube is clogged by the cuff 13. Among the constituent elements of the tracheostomy tube A, the surface of the lumen body 10, the inner surface of the airway securing lumen 10b, and the surface of the cuff 13 are coated with a coating layer (not shown) which exhibits surface lubricity in moisture.

In this construction, when it is intended to fit the tracheostomy tube A to the incision site (not shown) of a patient's trachea, first, the air in the cuff 13 is discharged (for example by pressing the cuff flat) to deflate the cuff and the surface of the lumen body 10 and the surface of the cuff 13 are then wetted to allow the coating layer of the surfaces to exhibit the surface lubricity. Next, the tracheostomy tube A is inserted into the trachea from its tip end portion and is held at a proper position. At this time, since insertion resistance is reduced due to the surface lubricity of the coating layer on the surface of the lumen body 10 and the surface of the cuff 13, the tracheostomy tube A is smoothly inserted into the trachea. Next, by injecting the air through the air injection portion 19a of the cuff tube 19, the cuff 13 is gradually inflated, that is, expanded.

As a result, the tracheostomy tube A is supported in the trachea in the state where the cuff 13 occludes the gap between the trachea and the tracheostomy tube. Then, by coupling a fixing belt (not shown) to the holes 17b and 17c of the arms 16b and 16c and extending the belt around the neck of the patient, the tracheostomy tube A does not depart from the trachea. If needed, by hooking a belt of another instrument onto the hooking pieces 12c and 12d of the coupling section 12, another instrument may be coupled to the tracheostomy tube A.

As a result, the patient can send the external air to the lungs through the trachea from the tracheostomy tube A, without any air passing through the nose or the throat of the patient. In addition, when inhaled air is discharged from the lungs, the air can be discharged externally from the trachea through the tracheostomy tube A, not through the nose or the throat. In use, when foreign substances such as sputum or foods are accumulated between the surface of the lumen body 10 and the trachea, a suction machine is coupled to the suction opening 18a of the suction-lumen tube 18 to suck out the foreign substances. Accordingly, the foreign substances such as sputum accumulated in the trachea can be sucked through the opening 14a of the suction lumen 14 and then discharged externally through the suction opening 18a.

In the course of using the tracheostomy tube A, the inner surface of the airway securing lumen 10b is maintained in moisture by vapor or the like at the time of the patient's respiration. As a result, the coating layer on the inner surface of the airway securing lumen 10b exhibits the surface lubricity and thus the inner surface of the airway securing lumen 10b is kept smooth. Therefore, it is possible to prevent the foreign substances such as sputum from being attached to and accumulated on the inner surface of the airway securing lumen 10b.

When the tracheostomy tube A is detached from the trachea for the purpose of replacement or repair of the tracheostomy tube A, first, the belt or the like of another instrument is removed and the fixing belt inserted into the holes 17b and 17c of the arms 16b and 16c is removed. Then, the air is discharged from the air injection portion 19a of the cuff tube 19, which allows the cuff to deflate, and the tracheostomy tube A is pulled out of the trachea in the state that the cuff 13 is contracted. In this case, it is possible to smoothly pull the tracheostomy tube A out of the trachea due to the surface lubricity of the coating layer on the surfaces of the lumen body 10 and the cuff 13.

As described above, in the tracheostomy tube A according to the present embodiment, the coating layer exhibiting the surface lubricity in moisture is formed on the surfaces of the lumen body 10 and the cuff 13. As a result, since the insertion resistance is reduced, it is possible to smoothly attach or detach the tracheostomy tube A to or from the trachea. In addition, since the coating layer exhibiting the surface lubricity in moisture is also formed on the inner surface of the airway securing lumen 10b, the foreign substances such as sputum or foods cannot be easily attached onto the inner surface of the airway securing lumen 10b. Therefore, it is possible to prevent the foreign substances such as sputum or foods from being accumulated in the lumen body 10.

In the tracheostomy tube A according to the present invention, a variety of materials may be used as the material for forming the coating layer exhibiting the surface lubricity in moisture. The lubricity or durability of the coating layer of the tracheostomy tube A having the coating layer made of a variety of materials will be described with reference to first to third embodiments and a first comparative example. Here, it was supposed that a base material of the tracheostomy tube A is a polyvinyl chloride resin and the thickness of the cuff 13 is 0.1 mm.

First Embodiment

A mixture solution obtained by adding 20 wt % of fluorine-containing acryl urethane silicon resin to a solution of 2-propanol/tetrahydrofuran (weight ratio=70:30) in which 2 wt % of methylvinyl ether maleic anhydride copolymer (product name: Gauntlets AN-169, made by ISP Co.) is dissolved was prepared. Then, the constituent base members of the tracheostomy tube A were dipped into the mixture solution, thereby coating the surface or the inner surface (inner surface of the airway securing lumen 10b) of the constituent base members of the tracheostomy tube A with the mixture solution. Thereafter, the tracheostomy tube A was obtained by immersing the constituent base members of the tracheostomy tube A in a 0.1N aqueous solution of sodium hydroxide and forming the coating layer on the surface and the inner surface of the constituent base members of the tracheostomy tube A.

Second Embodiment

A mixture solution obtained by adding 1 wt % of polyether-block-amide (product name: Pabex 3533, made by ATOFINA Chemicals Ltd. (changed to ARKEMA Yoshitomi Ltd. in 2004)) to a solution of 2-propanol/tetrahydrofuran (weight ratio=70:30) in which 2 wt % of methylvinyl ether maleic anhydride copolymer (product name: Gauntlets AN-169, made by ISP Corporation) is dissolved was prepared. Then, the constituent base members of the tracheostomy tube A were dipped into the mixture solution, thereby coating the surface or the inner surface (inner surface of the airway securing lumen 10b) of the constituent base members of the tracheostomy tube A with the mixture solution. Thereafter, the tracheostomy tube A was obtained by immersing the constituent base members of the tracheostomy tube A in a 0.1N aqueous solution of sodium hydroxide and forming the coating layer on the surface and the inner surface of the constituent base members of the tracheostomy tube A.

Third Embodiment

A mixture solution of 2-propanol/tetrahydrofuran (weight ratio=70:30) including 1 wt % of polyisocyanate (product name: Duranate D-101, made by Asahi Kasei Chemicals Corporation) and 2 wt % of polyurethane (product name: Decofrax, made by NOBEON Corporation) was prepared. Then, the constituent base members of the tracheostomy tube A were dipped into the mixture solution, thereby forming a basic coating layer on the surface or the inner surface (inner surface of the airway securing lumen 10b) of the constituent base members of the tracheostomy tube A. Next, a mixture solution of 5% polyvinyl pyrrolidone (K-90, made by GAF Corporation) and 2-propanol/tetrahydrofuran (weight ratio=70:30) was prepared. Thereafter, the tracheostomy tube A was obtained by dipping the constituent base members of the tracheostomy tube A in the mixture solution and coating the surface or the inner surface of the constituent base members of the tracheostomy tube A with the mixture solution to form the coating layer.

First Comparative Example

A mixture solution in which 20 wt % of fluorine-containing acryl urethane silicon resin was mixed with tetrahydrofuran was prepared. Then, the constituent base members of the tracheostomy tube A were dipped into the mixture solution, thereby coating the surface or the inner surface (inner surface of the airway securing lumen 10b) of the constituent base members of the tracheostomy tube A with the mixture solution. Thereafter, the tracheostomy tube A according to the first comparative example was obtained by immersing the constituent base members of the tracheostomy tube A in a 0.1N aqueous solution of sodium hydroxide and forming the coating layer on the surface and the inner surface of the constituent base members of the tracheostomy tube A.

When the tracheostomy tubes A according to the first to third embodiments were immersed in water, the coating layers formed on the surface or the inner surface of the tracheostomy tubes A all exhibited the lubricity at once. Accordingly, even when friction such as rubbing was applied to the coating layer, the coating layer was not peeled out of the constituent base members. The cuffs 13 of the tracheostomy tubes A were not melted in the mixture solution.

On the other hand, in the tracheostomy tube according to the first comparative example, a part of the cuff was melted in the solvent and thus when, the cuff was expanded by injecting the air thereto, the cuff was broken off sometimes. In addition, parts fused to each other appeared in the cuff and thus the cuff was not expanded in a predetermined shape sometimes. As a result, it could be said that the tracheostomy tubes A according to the first to third embodiments have quality, that is, lubricity and durability, more excellent than those of the tracheostomy tube according to the first comparative example.

In another embodiment, the mixture solution for forming the coating layer of the tracheostomy tubes A according to the first to third embodiments may contain a solvent including 2-propanol in which polyvinyl chloride resin has poor solubility or alcohol such as ethanol as a main component. In this case, without melting or damaging the cuff 13 of a thin film shape, it is possible to satisfactorily form the coating layer having excellent lubricity on the surface of the tracheostomy tube A or the inner surface of the lumen body 10 in which the airway securing lumen 10b is formed.

The present invention is not limited to the above-mentioned embodiments, but may be modified properly. For example, materials such as poly urethane, nylon, nylon elastomer, and the like may be used as the base material of the tracheostomy tube A, not limited to the polyvinylchloride resin. Further, the suction opening 18a of the suction section, the tube for a suction lumen 18, the suction lumen 14, and the opening 14a may be omitted. Furthermore, the shapes of the elements of the tracheostomy tube A or the material of the coating layer can be also properly modified without departing from the technical scope of the present invention.

What is claimed is:

1. A tracheostomy tube comprising:
   a lumen body having a circumferential wall which defines an airway securing lumen, the circumferential wall having an inner surface, an outer surface, a base end portion, and a tip end portion, wherein the airway securing lumen extends from the base end portion to the tip end portion;
   a connector section having a surface portion, which is formed at the base end portion of the lumen body;
   a cuff having an inner surface and an outer surface, which is formed on the outer surface of the tip end portion of the lumen body and which is expandable and contractible;
   a cuff-expanding lumen which is formed in the circumferential wall of the lumen body and which allows the surface portion of the connector section to communicate with the inner surface of the cuff; and
   a suction tube which is formed in the circumferential wall of the lumen body and which allows the surface portion of the connector section to communicate with the outer surface of the lumen body;
   wherein a coating layer exhibiting surface lubricity in moisture is formed on the outer surface of the lumen body, the outer surface of the cuff, and the inner surface of the lumen body in which the airway securing lumen is formed, and wherein the coating layer comprises a fluorine-containing acryl urethane silicon resin.

2. The tracheostomy tube of claim 1 wherein the coating layer comprises a mixture of at least two polymers, wherein the mixture of two polymers exhibits surface lubricity in moisture.

3. The tracheostomy tube of claim 1 wherein the coating layer consists essentially of a mixture of two polymers.

4. The tracheostomy tube of claim 1 wherein the coating layer comprises a mixture of the fluorine-containing acryl urethane silicon resin and at least one other polymer.

5. The tracheostomy tube of claim 4 wherein the coating layer comprises a mixture of the fluorine-containing acryl urethane silicon resin and a methyl vinyl ether maleic anhydride copolymer.

6. A tracheostomy tube comprising:
a lumen body having a circumferential wall which defines an airway securing lumen, the circumferential wall having an inner surface, an outer surface, a base end portion, and a tip end portion, wherein the airway securing lumen extends from the base end portion to the tip end portion;
a connector section having a surface portion, which is formed at the base end portion of the lumen body;
a cuff having an inner surface and an outer surface, which is formed on the outer surface of the tip end portion of the lumen body and which is expandable and contractible;
a cuff-expanding lumen which is formed in the circumferential wall of the lumen body and which allows the surface portion of the connector section to communicate with the inner surface of the cuff; and
a suction tube which is formed in the circumferential wall of the lumen body and which allows the surface portion of the connector section to communicate with the outer surface of the lumen body;
wherein a coating layer exhibiting surface lubricity in moisture is formed on the outer surface of the lumen body, the outer surface of the cuff, and the inner surface of the lumen body in which the airway securing lumen is formed, and wherein the coating layer comprises a polyether-block-amide.

7. The tracheostomy tube of claim 6 wherein the coating layer comprises a mixture of the polyether-block-amide and at least one other polymer.

8. The tracheostomy tube of claim 7 wherein the coating layer comprises a mixture of the polyether-block-amide and a methyl vinyl ether maleic anhydride copolymer.

9. A tracheostomy tube comprising:
a lumen body having a circumferential wall which defines an airway securing lumen, the circumferential wall having an inner surface, an outer surface, a base end portion, and a tip end portion, wherein the airway securing lumen extends from the base end portion to the tip end portion;
a connector section having a surface portion, which is formed at the base end portion of the lumen body;
a cuff having an inner surface and an outer surface, which is formed on the outer surface of the tip end portion of the lumen body and which is expandable and contractible;
a cuff-expanding lumen which is formed in the circumferential wall of the lumen body and which allows the surface portion of the connector section to communicate with the inner surface of the cuff; and
a suction tube which is formed in the circumferential wall of the lumen body and which allows the surface portion of the connector section to communicate with the outer surface of the lumen body;
wherein a coating layer exhibiting surface lubricity in moisture is formed on the outer surface of the lumen body, the outer surface of the cuff, and the inner surface of the lumen body in which the airway securing lumen is formed, and wherein the coating layer comprises a mixture including polyisocyanate and a mixture including polyvinyl pyrrolidone.

10. The tracheostomy tube of claim 9 wherein the coating layer further comprises polyurethane.

11. The tracheostomy tube of claim 1 wherein the coating layer is formed by applying a mixture including a solvent in which a material of the tracheostomy tube is not more than poorly soluble.

12. The tracheostomy tube of claim 11 wherein the main component of the solvent is alcohol.

* * * * *